(12) United States Patent
Meneghin et al.

(10) Patent No.: US 10,076,395 B2
(45) Date of Patent: Sep. 18, 2018

(54) PROSTHESIS HAVING A RADIOPAQUE ELEMENT

(75) Inventors: Alfredo Meneghin, Laval (FR); Xavier Bourges, Saint Etienne sur Chalaronne (FR); Julie Lecuivre, Le Bois d'Oingt (FR)

(73) Assignee: SOFRADIM PRODUCTION, Trevoux (FR)

( * ) Notice: Subject to any disclaimer, the term of this patent is extended or adjusted under 35 U.S.C. 154(b) by 84 days.

(21) Appl. No.: 13/810,510

(22) PCT Filed: Jul. 15, 2011

(86) PCT No.: PCT/EP2011/062148
§ 371 (c)(1),
(2), (4) Date: Mar. 8, 2013

(87) PCT Pub. No.: WO2012/007579
PCT Pub. Date: Jan. 19, 2012

(65) Prior Publication Data
US 2013/0158572 A1 Jun. 20, 2013

(30) Foreign Application Priority Data
Jul. 16, 2010 (FR) ..................... 10 55798

(51) Int. Cl.
*A61F 2/00* (2006.01)
*D04B 21/12* (2006.01)

(52) U.S. Cl.
CPC ............ *A61F 2/0063* (2013.01); *D04B 21/12* (2013.01); *A61F 2/0045* (2013.01);
(Continued)

(58) Field of Classification Search
CPC ........ A61F 2/0063; A61F 2/0045; A61F 2/02; A61F 2/0022; A61F 2/0009;
(Continued)

(56) References Cited

U.S. PATENT DOCUMENTS

| 3,054,406 A | 9/1962 | Usher |
| 3,276,448 A | 10/1966 | Kronenthal |

(Continued)

FOREIGN PATENT DOCUMENTS

| CN | 101489502 A | 7/2009 |
| DE | 19636961 A1 | 3/1998 |

(Continued)

OTHER PUBLICATIONS

International Search Report corresponding to International Application No. PCT/EP2011/062148, date of completion was Aug. 16, 2011 and dated Aug. 24, 2011; (2 pages).

(Continued)

*Primary Examiner* — Jocelin Tanner

(57) ABSTRACT

The present invention relates to a prosthesis (10) intended to be implanted at an implantation site, comprising i) at least one fabric called the base fabric (2) having at least one apertured surface (3), ii) and at least one patch (4) provided with at least one barb (5) projecting from one of its surfaces and grippingly fastening said patch to said apertured surface of said base fabric at a specific place on said surface, said patch comprising at least one radiopaque element. The invention also relates to a kit comprising a fabric and a patch.

11 Claims, 1 Drawing Sheet

Figure 1:
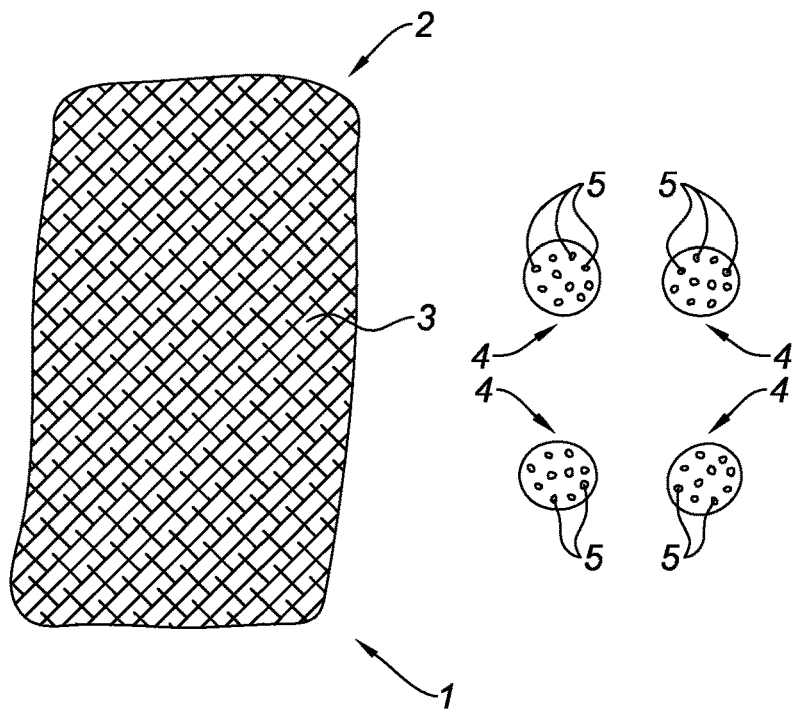

(52) U.S. Cl.
CPC ............... *A61F 2210/0004* (2013.01); *A61F 2250/0062* (2013.01); *A61F 2250/0085* (2013.01); *A61F 2250/0097* (2013.01); *A61F 2250/0098* (2013.01); *D10B 2403/0213* (2013.01); *D10B 2501/0632* (2013.01); *D10B 2509/08* (2013.01)

(58) Field of Classification Search
CPC .... A61F 2/0031; A61F 2/0036; A61F 2/0018; A61F 13/00; A61F 2013/00
USPC ............. 623/11.11, 23.72, 23.74; 57/80; 604/372, 373; 606/151, 148, 153, 139, 606/142, 228, 223, 229–231, 155, 213, 606/215; 600/36, 37; 602/41–45, 47, 48, 602/53, 55, 56
See application file for complete search history.

(56) References Cited

U.S. PATENT DOCUMENTS

| | | | |
|---|---|---|---|
| 3,887,699 A | 6/1975 | Yolles | |
| 4,767,628 A | 8/1988 | Hutchinson | |
| 4,931,546 A | 6/1990 | Tardy et al. | |
| 4,976,737 A | 12/1990 | Leake | |
| 5,116,357 A | 5/1992 | Eberbach | |
| 5,147,374 A | 9/1992 | Fernandez | |
| 5,195,542 A | 3/1993 | Gazielly et al. | |
| 5,201,745 A | 4/1993 | Tayot et al. | |
| 5,254,133 A | 10/1993 | Seid | |
| 5,258,000 A | 11/1993 | Gianturco | |
| 5,368,602 A * | 11/1994 | de la Torre | A61B 17/0057 602/44 |
| 5,370,650 A | 12/1994 | Tovey et al. | |
| 5,397,331 A | 3/1995 | Himpen | |
| 5,593,441 A | 1/1997 | Lichtenstein et al. | |
| 5,634,931 A | 6/1997 | Kugel | |
| 5,676,967 A | 10/1997 | Williams et al. | |
| 5,695,525 A | 12/1997 | Mulhauser et al. | |
| 5,702,416 A | 12/1997 | Kieturakis et al. | |
| 5,728,116 A * | 3/1998 | Rosenman | A61B 17/0401 606/151 |
| 5,743,917 A | 4/1998 | Saxon | |
| 5,766,246 A | 6/1998 | Mulhauser et al. | |
| 5,769,864 A | 6/1998 | Kugel | |
| 5,711,960 A | 7/1998 | Shikinami | |
| 5,916,225 A | 6/1999 | Kugel | |
| 5,919,232 A | 7/1999 | Chaffringeon et al. | |
| 5,922,026 A | 7/1999 | Chin | |
| 5,954,767 A * | 9/1999 | Pajotin | A61F 2/0063 606/215 |
| 6,004,333 A * | 12/1999 | Sheffield | A61F 2/0063 602/41 |
| 6,042,534 A | 3/2000 | Gellman et al. | |
| 6,090,116 A | 7/2000 | D'Aversa et al. | |
| 6,113,623 A | 9/2000 | Sgro | |
| 6,120,539 A | 9/2000 | Eldridge et al. | |
| 6,162,962 A | 12/2000 | Hinsch et al. | |
| 6,171,318 B1 | 1/2001 | Kugel et al. | |
| 6,174,320 B1 | 1/2001 | Kugel et al. | |
| 6,176,863 B1 | 1/2001 | Kugel et al. | |
| 6,180,848 B1 | 1/2001 | Flament et al. | |
| 6,197,935 B1 | 3/2001 | Doillon et al. | |
| 6,201,439 B1 | 4/2001 | Firmin et al. | |
| 6,214,020 B1 | 4/2001 | Mulhauser et al. | |
| 6,224,616 B1 | 5/2001 | Kugel | |
| 6,241,768 B1 | 6/2001 | Agarwal et al. | |
| 6,258,124 B1 | 7/2001 | Darois et al. | |
| 6,264,702 B1 | 7/2001 | Ory et al. | |
| 6,267,772 B1 | 7/2001 | Mulhauser et al. | |
| 6,270,530 B1 | 8/2001 | Eldridge et al. | |
| 6,270,792 B1 | 8/2001 | Guillemet et al. | |
| 6,280,453 B1 | 8/2001 | Kugel et al. | |
| 6,287,316 B1 | 9/2001 | Agarwal et al. | |
| 6,290,708 B1 | 9/2001 | Kugel et al. | |
| 6,306,079 B1 | 10/2001 | Trabucco | |
| 6,319,264 B1 | 11/2001 | Törmälä | |
| 6,383,201 B1 | 5/2002 | Dong | |
| 6,387,041 B1 * | 5/2002 | Harari | A61B 17/0401 600/30 |
| 6,425,924 B1 | 7/2002 | Rousseau | |
| 6,447,551 B1 | 9/2002 | Goldmann | |
| 6,485,503 B2 | 11/2002 | Jacobs et al. | |
| 6,500,777 B1 | 12/2002 | Wiseman et al. | |
| 6,517,564 B1 * | 2/2003 | Grafton | A61B 17/0401 606/213 |
| 6,596,002 B2 | 7/2003 | Therin et al. | |
| 6,610,006 B1 | 8/2003 | Amid et al. | |
| 6,616,685 B2 | 9/2003 | Rousseau | |
| 6,645,226 B1 | 11/2003 | Jacobs et al. | |
| 6,652,595 B1 | 11/2003 | Nicolo | |
| 6,669,735 B1 | 12/2003 | Pelissier | |
| 6,712,859 B2 | 3/2004 | Rousseau et al. | |
| 6,736,823 B2 | 5/2004 | Darois et al. | |
| 6,736,854 B2 | 5/2004 | Vadurro et al. | |
| 6,737,371 B1 | 5/2004 | Planck et al. | |
| 6,746,458 B1 | 6/2004 | Cloud | |
| 6,755,868 B2 | 6/2004 | Rousseau | |
| 6,790,213 B2 | 9/2004 | Cherok et al. | |
| 6,800,082 B2 | 10/2004 | Rousseau | |
| 6,872,227 B2 | 3/2005 | Sump et al. | |
| 6,926,723 B1 | 8/2005 | Mulhauser et al. | |
| 7,011,688 B2 | 3/2006 | Gryska et al. | |
| 7,021,086 B2 | 4/2006 | Ory et al. | |
| 7,022,358 B2 | 4/2006 | Eckmayer et al. | |
| 7,041,868 B2 | 5/2006 | Greene et al. | |
| 7,060,103 B2 | 6/2006 | Can, Jr. et al. | |
| 7,070,558 B2 | 7/2006 | Gellman et al. | |
| 7,087,065 B2 | 8/2006 | Ulmsten et al. | |
| 7,094,261 B2 | 8/2006 | Zotti et al. | |
| 7,101,381 B2 | 9/2006 | Ford et al. | |
| 7,156,804 B2 | 1/2007 | Nicolo | |
| 7,156,858 B2 | 1/2007 | Schuldt-Hempe et al. | |
| 7,252,837 B2 | 8/2007 | Guo et al. | |
| 7,279,177 B2 | 10/2007 | Looney et al. | |
| 7,291,294 B2 | 11/2007 | Lewis | |
| 7,331,199 B2 | 2/2008 | Ory et al. | |
| 7,393,319 B2 | 7/2008 | Merade et al. | |
| 7,404,199 B2 | 7/2008 | Arneson et al. | |
| 7,556,598 B2 | 7/2009 | Rao | |
| 7,594,921 B2 | 9/2009 | Browning | |
| 7,614,258 B2 | 11/2009 | Cherok et al. | |
| 7,732,354 B2 | 6/2010 | Fricke et al. | |
| 7,785,334 B2 | 8/2010 | Ford et al. | |
| 7,806,905 B2 | 10/2010 | Ford et al. | |
| 7,824,420 B2 | 11/2010 | Eldridge et al. | |
| 7,828,854 B2 | 11/2010 | Rousseau et al. | |
| 7,832,406 B2 * | 11/2010 | Ellis et al. | 128/898 |
| 7,869,861 B2 | 1/2011 | De la Barrera | |
| 7,900,484 B2 | 3/2011 | Cherok et al. | |
| 8,100,924 B2 | 1/2012 | Browning | |
| 8,123,817 B2 | 2/2012 | Intoccia et al. | |
| 8,157,821 B2 | 4/2012 | Browning | |
| 8,157,822 B2 | 4/2012 | Browning | |
| 8,182,545 B2 | 5/2012 | Cherok et al. | |
| 8,206,632 B2 | 6/2012 | Rousseau et al. | |
| 8,215,310 B2 | 7/2012 | Browning | |
| 8,682,052 B2 | 3/2014 | Fitz | |
| 2002/0077661 A1 | 6/2002 | Saadat | |
| 2002/0087174 A1 | 7/2002 | Capello | |
| 2002/0099344 A1 | 7/2002 | Hessel et al. | |
| 2002/0131988 A1 | 9/2002 | Foster et al. | |
| 2002/0165601 A1 | 11/2002 | Clerc | |
| 2003/0078602 A1 * | 4/2003 | Rousseau | 606/151 |
| 2003/0130745 A1 | 7/2003 | Cherok et al. | |
| 2004/0054376 A1 * | 3/2004 | Ory | A61F 2/0063 606/151 |
| 2004/0098118 A1 | 5/2004 | Granada et al. | |
| 2004/0215219 A1 | 10/2004 | Eldridge et al. | |
| 2004/0220591 A1 * | 11/2004 | Bonutti | 606/151 |
| 2004/0224007 A1 | 11/2004 | Zhang | |
| 2004/0230208 A1 * | 11/2004 | Shayani | A61B 17/064 606/151 |
| 2005/0113849 A1 | 5/2005 | Popadiuk et al. | |

(56) References Cited

U.S. PATENT DOCUMENTS

| | | |
|---|---|---|
| 2005/0240261 A1 | 10/2005 | Rakos et al. |
| 2005/0244455 A1 | 11/2005 | Greenawalt |
| 2005/0261782 A1 | 11/2005 | Hoganson |
| 2006/0034887 A1 | 2/2006 | Pelissier |
| 2006/0116696 A1 | 6/2006 | Odermatt et al. |
| 2006/0121078 A1 | 6/2006 | Trogolo et al. |
| 2006/0188546 A1 | 8/2006 | Giroux |
| 2006/0195010 A1* | 8/2006 | Arnal et al. .............. 600/30 |
| 2006/0224038 A1 | 10/2006 | Rao |
| 2006/0253203 A1 | 11/2006 | Alvarado |
| 2006/0282103 A1 | 12/2006 | Fricke et al. |
| 2007/0088391 A1 | 4/2007 | McAlexander et al. |
| 2007/0129736 A1 | 6/2007 | Solecki |
| 2007/0198040 A1 | 8/2007 | Buevich et al. |
| 2007/0244548 A1 | 10/2007 | Myers et al. |
| 2007/0260268 A1 | 11/2007 | Bartee et al. |
| 2008/0004714 A1* | 1/2008 | Lieberman ............. A61B 17/58 623/23.76 |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0147200 A1 | 6/2008 | Rousseau et al. |
| 2008/0161837 A1 | 7/2008 | Toso et al. |
| 2008/0172071 A1 | 7/2008 | Barker |
| 2008/0199506 A1 | 8/2008 | Hones et al. |
| 2008/0255593 A1 | 10/2008 | St-Germain |
| 2009/0036996 A1 | 2/2009 | Roeber |
| 2009/0069826 A1 | 3/2009 | Walther et al. |
| 2009/0082792 A1 | 3/2009 | Koyfman et al. |
| 2009/0105526 A1 | 4/2009 | Piroli Torelli et al. |
| 2009/0125107 A1 | 5/2009 | Maxwell |
| 2009/0142385 A1 | 6/2009 | Gross et al. |
| 2009/0163936 A1 | 6/2009 | Yang et al. |
| 2009/0171377 A1 | 7/2009 | Intoccia et al. |
| 2009/0187197 A1 | 7/2009 | Roeber et al. |
| 2009/0192530 A1 | 7/2009 | Adzich et al. |
| 2009/0198260 A1 | 8/2009 | Ford et al. |
| 2009/0270999 A1 | 10/2009 | Brown |
| 2009/0276057 A1 | 11/2009 | Trabucco et al. |
| 2009/0281558 A1* | 11/2009 | Li ............................. 606/151 |
| 2009/0299538 A1 | 12/2009 | Suzuki |
| 2009/0326676 A1 | 12/2009 | Dupic et al. |
| 2010/0003308 A1 | 1/2010 | Tapolsky et al. |
| 2010/0089409 A1 | 4/2010 | Bertagnoli |
| 2010/0094404 A1 | 4/2010 | Greenhalgh |
| 2010/0160375 A1 | 6/2010 | King |
| 2010/0241145 A1* | 9/2010 | Cook ............................. 606/151 |
| 2010/0286716 A1 | 11/2010 | Ford et al. |
| 2010/0312043 A1 | 12/2010 | Goddard |
| 2010/0318108 A1 | 12/2010 | Datta et al. |
| 2011/0144667 A1 | 1/2011 | Horton et al. |
| 2011/0082330 A1 | 4/2011 | Deitch |
| 2011/0082478 A1* | 4/2011 | Glick et al. .............. 606/148 |
| 2011/0238094 A1 | 9/2011 | Thomas et al. |
| 2011/0257666 A1 | 10/2011 | Ladet et al. |
| 2011/0264120 A1 | 10/2011 | Bayon et al. |
| 2011/0265283 A1 | 11/2011 | Duncan |
| 2011/0293688 A1 | 12/2011 | Bennett et al. |
| 2011/0295284 A1* | 12/2011 | Purdue ..................... A61F 2/08 606/151 |
| 2012/0010637 A1 | 1/2012 | Stopek et al. |
| 2012/0016388 A1 | 1/2012 | Houard et al. |
| 2012/0029537 A1 | 2/2012 | Mortarino |
| 2012/0029540 A1 | 2/2012 | Adams |
| 2012/0053602 A1 | 3/2012 | Adzich et al. |
| 2012/0065727 A1 | 3/2012 | Reneker et al. |
| 2012/0082712 A1 | 4/2012 | Stopek et al. |
| 2012/0109165 A1 | 5/2012 | Mathisen et al. |
| 2012/0116423 A1 | 5/2012 | Gleiman et al. |
| 2012/0116425 A1 | 5/2012 | Intoccia et al. |
| 2012/0150204 A1 | 6/2012 | Mortarino et al. |
| 2012/0179175 A1 | 7/2012 | Hammell |
| 2012/0179176 A1 | 7/2012 | Wilson et al. |
| 2012/0239063 A1 | 9/2012 | Lee |
| 2012/0259348 A1 | 10/2012 | Paul |
| 2013/0060263 A1 | 3/2013 | Bailly et al. |

FOREIGN PATENT DOCUMENTS

| | | |
|---|---|---|
| EP | 1 674 048 | 6/2006 |
| EP | 2 016 956 A2 | 1/2009 |
| EP | 2 404 571 | 1/2012 |
| FR | 2 601 371 | 1/1988 |
| FR | 2 857 851 | 1/2005 |
| WO | WO 93/11805 | 6/1993 |
| WO | WO 98/06355 A1 | 2/1998 |
| WO | WO 99/51163 | 10/1999 |
| WO | WO 02/34304 | 5/2002 |
| WO | WO 03/007847 | 1/2003 |
| WO | 03037215 A2 | 5/2003 |
| WO | WO 2006/020922 A2 | 2/2006 |
| WO | WO 2006/036967 | 4/2006 |
| WO | WO 2006/102374 A2 | 9/2006 |
| WO | WO 2007/025266 A2 | 3/2007 |
| WO | WO 2008/127411 | 10/2008 |
| WO | WO 2009/075786 | 6/2009 |
| WO | WO 2011/038740 | 4/2011 |
| WO | WO 0180788 | 11/2011 |
| WO | WO 2010/093333 | 8/2012 |

OTHER PUBLICATIONS

Japanese Office Action corresponding to Japanese Patent Application No. 2013-519113 dated Dec. 16, 2015, together with English translation, 7 pages.

Japanese Office Action corresponding to Japanese Patent Application No. 2013-519113 dated Sep. 14, 2015.

Chinese Office Action, Application No. 201180042606.6 dated May 20, 2015.

Canadian Office Action dated Jun. 8, 2017 in corresponding Canadian Patent Application No. 2,805,497, 3 pages.

* cited by examiner

PROSTHESIS HAVING A RADIOPAQUE ELEMENT

CROSS-REFERENCE TO RELATED APPLICATIONS

This application is a U.S. National Stage Application filed under 35 U.S.C. § 371(a) of International Application No. PCT/EP2011/062148 filed Jul. 15, 2011, which claims the benefit of and priority to French Patent Application Serial No. 10/55798 filed Jul. 16, 2010, the entire contents of which are incorporated by reference herein.

The present invention relates to a prosthesis based on a fabric and comprising information means for the surgeon, designed to facilitate the implantation of the prosthesis in a specified disposition and/or to determine the position of the prosthesis, once this has been implanted, by radioscopy.

Many prostheses, such as for example abdominal wall reinforcements or urinary incontinence pads, take the form of a piece of biocompatible fabric, which may or may not be accompanied by additional elements such as, for example, a coating in the form of a film, reinforcing elements, a set of needles, etc. The piece of fabric of these prostheses are often of symmetrical shape. This is in particular the case of prostheses for reinforcing walls, for example abdominal walls, these being widely used in the surgical field and designed for treating hernias, by filling, either temporarily or definitely, a tissue failure. These prostheses may be of various shapes: rectangular, round, oval, etc., depending on the anatomical structure to which they have to adapt. Some of these prostheses are made from entirely biodegradable yarns and are intended to disappear after having carried out their reinforcing role until cell colonization takes place and tissue rehabitation takes over. Other prostheses comprise non-biodegradable yarns and are intended to remain permanently in the patient's body.

In any case, for safety reasons, these prostheses must often be positioned in a specific and very precise way with respect to the surrounding organs at the moment of implantation. Thus, it is sometimes necessary to provide these prostheses with markers or information means for the purpose of providing the surgeon with indications about the position of the prosthesis, in particular once said prosthesis has been implanted.

Thus, depending on the environment of the implantation site, for example in the presence of viscera, soft tissue, etc., it may be important to give the surgeon indications at a given place on the fabric, so that he can position the piece of fabric in a particular orientation or else position a certain region of the prosthesis so as to face said organ or on the contrary to be as far as possible away from said organ, etc.

To be able to identify the position of an implanted prosthesis, a radiopaque element with which the prosthesis is provided is used so as to be able subsequently to monitor it by radioscopy. The term "radiopaque element" is understood, according to the present invention, to mean an opaque element which is not penetrated by X-rays or by ionizing radiation and which can be seen by radiography or by radioscopy.

However, providing a prosthesis with a radiopaque element is not anodyne. For the purpose of minimizing the presence of a radiopaque substance within the body of a patient to the maximum, it would be desirable for the surgeon to be able to decide what amount of radiopaque elements he wishes to introduce into the prosthesis and at what point(s) on the prosthesis. It would be advantageous for the surgeon to have a means for easily and rapidly providing a prosthesis with one or more radiopaque elements, for example just before implantation.

Thus, there remains a need to be able to provide the fabric of a prosthesis with radiopaque elements reliably and rapidly without jeopardizing the effectiveness both of said radiopaque elements and the prosthesis itself.

The aim of the present invention is to meet this need by providing a prosthesis based on a fabric, this being provided with radiopaque elements easy to install on said fabric, and having no negative effect on the positioning of the prosthesis and on its effectiveness.

A first aspect of the present invention is a prosthesis intended to be implanted at an implantation site, comprising i) at least one fabric called the base fabric having at least one apertured surface, ii) and at least one patch provided with at least one barb projecting from one of its surfaces and grippingly fastening said patch to said apertured surface of said base fabric at a specific place on said surface, said patch comprising at least one radiopaque element.

The term "fabric" is understood in the context of the present application to mean any fabric obtained by an arrangement or assembly of biocompatible yarns, fibres, monofilaments and/or multifilaments, such as a knitted, woven, braided or non-woven fabric, and having two opposed surfaces.

At least one of the surfaces of the base fabric of the prosthesis according to the invention is apertured. The term "apertured surface" is understood according to the present application to mean that said surface of the fabric comprises openings, cavities, pores or holes that are open to the outside. Such openings promote the penetration of cells into the fabric and therefore cell recolonization of the prosthesis after implantation. As will become apparent in the rest of the description, the openings in the apertured surface of the base fabric of the prosthesis according to the invention have a size making them capable of receiving and retaining, by their walls formed by the yarns constituting the fabric, the barb or barbs of the patch or patches of the prosthesis according to the invention.

The prosthesis according to the invention may be produced in a particularly simple and rapid manner. Specifically, the base fabric of the prosthesis does not have to undergo any particular treatment in order to include a radiopaque element. It is sufficient to provide the fabric with one or more patches that may for example be manufactured from a gripping fabric comprising at least one radiopaque yarn and are grippingly fastened to the base fabric at a particular place which will provide the surgeon with suitable information regarding the position of the prosthesis by taking a radioscopic image of the prosthesis once it has been implanted into the patient.

The prosthesis according to the invention, although provided with radiopaque elements, loses none of the initial properties of the base fabric. In particular, when the patch is made of an apertured gripping fabric comprising a radiopaque yarn, the apertured surface of the base fabric of the prosthesis according to the invention maintains its good cell recolonization capability.

The prosthesis according to the invention may comprise a plurality of patches as described above, these being grippingly fastened at specific places on the apertured surface of the base fabric.

Thus, for a rectangular or square base fabric, the surgeon may place a patch at each corner of the fabric so as to be more easily able to determine the position of the entire prosthesis once it has been implanted, for example by means of a first postoperative radioscopic image produced just after implantation and then taking one or more other radioscopic images, for example several months after the implantation, the comparison between the various radioscopic images allowing the surgeon to see if the prosthesis has migrated or if it has become deformed, for example by reduction or contraction of the base fabric.

The base fabric of the prosthesis according to the invention may have its two surfaces apertured. In such a case, one or more patches may be grippingly fastened to each of the two surfaces of the fabric, such a configuration making it possible for the thickness of the prosthesis, and therefore for example the state of its integrity, to be determined radioscopically several weeks or months after implantation.

The base fabric of the prosthesis according to the invention may be any fabric based on biocompatible yarns, filaments or fibres, such as a woven, a non-woven, a braid, a knit or a combination of the latter, provided that at least one of its surfaces is apertured.

The yarns, fibres or filaments and/or multifilaments forming the base fabric according to the invention may be made of any biocompatible material, whether biodegradable or not.

The term "biodegradable" or "bioresorbable" is understood in the context of the present application to mean the characteristic whereby a material is absorbed and degraded by biological tissues and disappears in vivo after a specified period of time which may vary, for example, from a few hours to several months, depending on the chemical nature of the material.

Thus, the biodegradable materials suitable for the yarns of the base fabric of the present invention may be chosen from polylactic acid (PLA), polyglycolic acid (PGA), oxidized cellulose, chitosan, polyphosphazene, polycaprolactone (PCL), polydioxanone (PDO), trimethylene carbonate (TMC), polyvinyl alcohol (PVA), polyhydroxyalkanoates (PHAs), polyamides, polyethers, copolymers thereof and blends thereof. Non-biodegradable materials suitable for the yarns of the base fabric of the present invention may be chosen from polyethylene terephthalate (PET), polyamides, aramids, expanded polytetrafluoroethylene, polyurethane, polyvinylidene fluoride (PVDF), butyl ester polymers, PEEK (polyetheretherketone), polyolefins (such as polyethylene or polypropylene), copper alloys, silver or platinum alloys, medical grades of steel such as medical-grade stainless steel, and combinations thereof.

In one embodiment of the invention, the base fabric is a knit: a knit, because of the meshes that make up the knit, provides apertured surfaces that are particularly well suited for the prosthesis according to the invention. The knit may be two-dimensional or three-dimensional.

The term "two-dimensional knit" is understood in the context of the present application to mean a knit having two opposed surfaces linked together by meshes but devoid of a spacer giving them a certain thickness: such a knit may for example be obtained by knitting yarns on a warp or Raschel knitting machine using two needle-guide bars. Examples of knitting two-dimensional knits suitable for the present invention, with at least one apertured surface, are given in document WO 2009/071998.

The term "three-dimensional knit" is understood according to the present application to mean a knit having two opposed surfaces linked together by a spacer giving the knit a significant thickness, said spacer itself being formed from additional linking yarns in addition to the yarns forming the two surfaces of the knit. Such a knit may for example be obtained on a double bed warp or Raschel knitting machine using several needle-guide bars. Examples of knitting three-dimensional knits suitable for the present invention, with at least one apertured surface, are given in the documents WO 99/05990, WO 2009/031035 and WO 2009/071998.

The base fabric of the invention may be a porous fabric or knit, i.e. one having cavities, pores or holes, not only on its surfaces but also within its thickness, these cavities, pores or holes being able to constitute channels emerging on either side of the fabric. Such a porous fabric allows better tissue integration, it being possible for cells to gain access to the interior of the fabric forming for example an abdominal wall reinforcement.

For example, the pattern of the base fabric may determine, within the thickness of the latter, a multiplicity of transverse cavities or channels, approximately parallel to one another, emerging on either side of said fabric on its two respective apertured surfaces, giving the fabric a "honeycomb" structure for example.

The patch or patches of the prosthesis according to the invention may be made of any biocompatible material and comprise at least one radiopaque element.

The radiopaque element may be made of any biocompatible radiopaque material. Examples of radiopaque materials that are particularly suitable for the invention are gold, palladium, tantalum, chromium, silver, zirconian, tungsten, platinum, barium sulphate ($BaSO_4$), bismuth oxide ($Bi_2O_3$), iodine and derived products, gadolinium, aluminosilicates, biocompatible phosphocalcic ceramics, such as for example hydroxyapatite or tricalcium phosphate, and mixtures thereof.

The patch or patches of the prosthesis according to the invention may have any shape imaginable, for example a geometric shape such as an oval, round or rectangular shape, or a graphical shape, such as an arrow or a symbol: in general, for the sake of minimizing the presence of foreign matter in the patient's body to the maximum, the patches have a size suitable for the necessary dose of radiopaque elements in order to make it detectable by radioscopy, said dose remaining well below the toxicity threshold dose for the radiopaque element. Thus, the amount of radiopaque element is adjusted according to the desired radiopacity for the radiography.

The patch or patches of the prosthesis according to the invention are provided with at least one, and preferably several, barbs projecting from one of their surfaces. These barbs may project from said surface substantially perpendicular to the plane of said surface or alternatively along one or more planes inclined to the plane of said surface. These barbs are intended to function as fastening means, by penetrating into the openings and intermeshing in the yarns forming the openings of the apertured surface or surfaces of the base fabric of the prosthesis according to the invention due to the effect of the pressure exerted on a patch towards the base fabric. Advantageously, these barbs may also be withdrawn, by pulling on the patch, which can then be repositioned elsewhere on the apertured surface of the base fabric, if required, at the moment of manufacture of the prosthesis according to the invention.

Thus, a patch may be grippingly fastened, if necessary temporarily, to the base fabric of the prosthesis according to the invention. Thus, in one embodiment, the barb or barbs grippingly fasten the patch or patches to the apertured surface of the base fabric in a repositionable manner.

Alternatively, it is possible to fix the patch or patches to the apertured surface of the base fabric definitely by adding a spot of adhesive or a suture stitch between the patch and the base fabric.

The barbs are made of a biocompatible material, which may or may not be identical to the material forming the body of the patch. In one embodiment of the invention, the barbs are made of a radiopaque material and constitute the radiopaque elements of the patches.

The patches of the prosthesis according to the invention may be produced by the injection moulding of a biocompatible thermoplastic.

In a preferred embodiment, the patches of the prosthesis according to the invention are made of a gripping fabric.

In the present application, the term "gripping fabric" is understood to mean a fabric having, on at least one of its surfaces, a plurality of hooks or barbs, arranged in a regular or random fashion, these projecting substantially perpendicular to said surface and being capable of penetrating the surface or the thickness of an apertured fabric on which it is applied. One example of a known gripping fabric is the gripping part of a "Velcro®" system. Thus, the barbs of the patches according to the invention may be formed from yarns, for example thermoplastic monofilament yarns, coming directly from the arrangement of yarns forming the patch. Such fabrics and barbs, and their manufacturing process, are for example described in the patent applications WO 01/81667, DE 198 32 634 or in the U.S. Pat. Nos. 6,596,002 and 5,254,133.

Alternatively, the barbs of the gripping fabric may be any hooks made of any biocompatible material, fastened to the arrangement of yarns forming said fabric, whether these hooks had been incorporated into said fabric during manufacture (braiding, knitting, weaving, etc.) of said arrangement of yarns or had been attached afterwards.

In a preferred embodiment, the barbs stem from the yarns used for knitting the gripping fabric. For example, the gripping fabric may comprise in general a lap of monofilaments initially forming small loops on the outside of said lap, each loop giving rise to two barbs projecting perpendicular to said lap after partial melting of the thermoplastic yarn initially forming the loop, as described in WO 01/81667.

Thus, the gripping fabric forming a patch of the prosthesis according to the invention may include some of its constituent yarns formed from a radiopaque material. These yarns may be those for forming the barbs of the gripping fabric or those forming the body of the gripping fabric, or else a combination of the two. In such an embodiment, the radiopaque element consists of one or more yarns forming the gripping fabric.

Preferably, the length of the barbs is defined so as to penetrate into and catch onto the apertured surface of the base fabric, preferably in a limited manner, that is to say if possible without passing from one side of the base fabric to the other.

A prosthesis according to the invention provided with radiopaque elements is thus very easy to produce, on the operating site, by the surgeon himself, just before carrying out the implantation procedure.

For example, it is sufficient for the surgeon to make the patches comprising the radiopaque elements grip the base fabric at the desired places by means of their barbs; moreover, it is also easy for the surgeon to remove these patches once they have been grippingly fastened and then to refasten them at more suitable places in the event of an error when first fastening them.

In a preferred embodiment, the gripping fabric used is itself apertured and/or porous, as defined above. Thus, once the patch has been grippingly fastened to the apertured surface of the base fabric, it in no way obstructs the openings in the apertured surface of the base fabric, thereby preserving its good cell recolonization capability. For example, the fabric structure of the patch comprises or defines, on its two surfaces, including that having the barbs, open pores having, for example, a diameter between 0.4 and 5 mm. In one embodiment, the patch may be provided with barbs on both its surfaces.

In one embodiment of the invention, the patch is made of a gripping fabric as described in WO 01/81667 and comprises at least one of its constituent yarns made of a radiopaque material. Examples of yarns made of radiopaque material that are particularly suitable for producing the patches of the prosthesis according to the present invention are for example those described in document U.S. Pat. No. 7,465,489.

For example, each barb may have a length of between 1 and 2 mm and the barb density may range from 30 to 50 barbs per square centimeter: such a density makes it possible for the patch to be grippingly fastened to the base fabric and/or easily removed therefrom so as to be repositioned if so required.

Alternatively or in combination, the radiopaque element may take the form of a coating made of a radiopaque material deposited on at least one surface of the patch. For example, it is possible to coat at least one surface of the patch, whether or not this is made of gripping fabric, with a radiopaque coating by chemical vapour deposition (CVD) or possibly plasma-enhanced chemical vapour deposition (PECVD) of radiopaque compounds as described above, in particular those chosen from gold, palladium, tantalum, chromium, silver, zirconian and mixtures thereof.

In one embodiment, said radiopaque element is in the form of a coating made of a radiopaque material, for example gold, deposited on each surface of the patch by plasma-enhanced chemical vapour deposition.

In another embodiment, the radiopaque element may be imprisoned in a matrix, for example a polypropylene matrix, forming a film which is bonded to one surface of the patch.

When such a gripping fabric in the form of a patch is applied, barbs to the front, on the apertured surface of the base fabric, the barbs engage in the meshes and between the yarns of the base fabric, and lock the patch onto the apertured surface of the base fabric. This locking effect, which is effective even in a liquid medium, is sufficient to fix the patch to the base fabric, while still allowing the patch to be unfastened so as to adjust its position relative to the base fabric, if so required.

Another aspect of the present invention is a kit comprising:

at least one fabric called the base fabric and having at least one apertured surface, designed to be implanted at an implantation site, as defined above; and at least one patch provided with at least one barb projecting from one of its surfaces and comprising at least one radiopaque element, said barb or barbs being designed for grippingly fastening said patch to said apertured surface of said base fabric at a specific place on said surface. The patch of the kit according to the invention may be as described above. The kit according to the invention may comprise a plurality of patches as described above.

Figure 2:
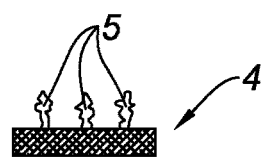
Figure 3:
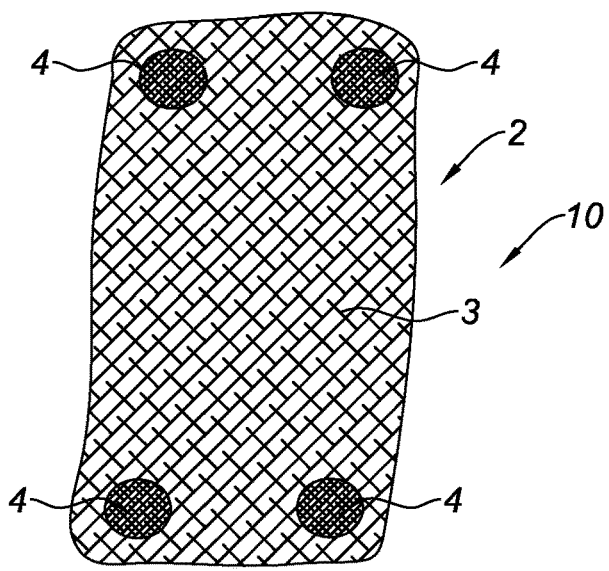

The advantages of the present invention will become more clearly apparent in the light of the following description and the appended drawings in which:

FIG. 1 is a top view of a kit according to the invention;
FIG. 2 is a cross-sectional view of a patch of a prosthesis according to the invention; and FIG. 3 is a top view of a prosthesis according to the invention.

Referring usefully to FIG. 1, a kit according to the present invention is shown in general by the reference 1. The kit 1 comprises a base fabric in the form of a piece of fabric 2 of rectangular overall shape. This piece of fabric 2 may have an area ranging from 4 to 1600 cm$^2$ and may advantageously be used for repairing an abdominal wall hernia. The piece of fabric 2 has two surfaces, an apertured surface 3 of which is visible in the figure.

Such a fabric with at least one apertured surface may be obtained using the following method: a three-dimensional knit is produced on a 22-gauge Raschel knitting machine using six needle-guide bars threaded one full/one empty with polyethylene terephthalate (PET) multifilament yarns (50 dtex; 22 filaments), using the following schemes, according to ISO 11676:

Bar 1: 1.2.1.1/1.0.1.1/1.2.1.1/1.0.1.1/1.2.2.2/3.2.2.2/1.2.2.2/3.2.2.2//

Bar 2: 1.2.2.2/3.2.2.2/1.2.2.2/3.2.2.2/1.2.1.1/1.0.1.1/1.2.1.1/1.0.1.1//

Bar 3: 0.1.0.1/0.0.0.0//

Bar 4: 0.1.0.1/0.0.0.0//

Bar 5: 1.1.0.1/1.1.2.1/1.1.0.1/1.1.2.1/2.2.2.3/2.2.2.1/2.2.2.3/2.2.2.1//

Bar 6: 2.2.2.3/2.2.2.1/2.2.2.3/2.2.2.1/1.1.0.1/1.1.2.1/1.1.01/1.1.2.1//

Bars 1 and 2 form one surface of the fabric, bars 5 and 6 form the opposite surface of the fabric and bars 3 and 4 form the spacer linking the two surfaces together.

Such a construction results in a three-dimensional knit having openings measuring about 2.5×1.7 mm on both its surfaces.

FIG. 1 also shows four patches 4 each taking the overall form of a disc. Each of these patches is provided with barbs 5 projecting perpendicular to one of their surfaces, as shown in FIG. 2, which is a cross-sectional view of a patch 4.

In this example, the patches 4 are made of a gripping fabric obtained in the following manner: a knit is produced on a 24-gauge weft knitting machine using 3 needle-guide bars. Bars 1 and 2, intended to form the body of the gripping fabric, are threaded one full/one empty with 0.09 mm diameter polyethylene terephtalate (PET) monofilament yarns according to the following schemes, according to ISO 11676:

Bar 1: 1.0/0.1//

Bar 2: 4.5/1.0//.

Bar 3, intended to form the monofilament lap resulting in the barbs is threaded 1 full/3 empty with a 0.15 mm diameter polylactic acid (PLA) monofilament yarn according to the following scheme, according to ISO 11676:

Bar 3: 3.4/0.0/2.1/5.5//.

The barbs are then produced by melting the loops of the lap produced by bar 3 according to the method described in WO 01/81667.

Both surfaces of the gripping fabric are then coated with gold by plasma-enhanced chemical vapour deposition (PECVD).

Next, the resulting coated gripping fabric is cut into four patches: these patches may have an area ranging for example from 0.5 to 6 cm$^2$, depending on the desired radiopacity for the radiography.

FIG. 3 shows a prosthesis 10 according to the invention produced from the kit 1 of FIG. 1. To produce the prosthesis 10, the four patches 4, with the barbs 5 directed towards the apertured surface 3 of the piece of base fabric 2, have simply been applied and pressure exerted thereon. The four patches 4 were applied at specific places on the apertured surface 3 of the base fabric, namely each at one corner of the base fabric 2, so that the surgeon can easily determine the position of the prosthesis by radioscopy once said prosthesis has been implanted. The position of the prosthesis 10 within the patient's body may thus be checked several weeks or months after implantation.

The prosthesis 10 was thus produced in a simple and particularly rapid manner. It may especially be produced easily by the surgeon himself just before implantation.

In a non-illustrated embodiment, the four patches may each comprise a yarn made of radiopaque material defining a particular shape, for example a circle, a cross, a triangle and so on, so that the surgeon may determine exactly which corner of the prosthesis is positioned at which place.

The invention claimed is:

1. A prosthesis comprising:
   i) at least one base fabric having at least one apertured surface which promotes penetration of cells into the base fabric and cell recolonization of the prosthesis after implantation,
   ii) and a plurality of repositionable gripping fabrics separate from the at least one base fabric, each repositionable gripping fabric in the form of a disc having a first apertured surface, a second surface opposite the first surface, at least one radiopaque element, and at least one barb projecting from the second surface of the repositionable gripping fabric and designed to grippingly fasten the repositionable gripping fabric to a first specific place on the at least one apertured surface of the at least one base fabric and is easily removed therefrom so as to be repositioned and refastened on a second specific place on the at least one apertured surface of the at least one base fabric, wherein each gripping fabric has an area ranging from 0.5 to 6 cm$^2$ and the first apertured surface promotes penetration of cells and preserves the cell recolonization of the prosthesis when the second surface of the gripping fabric is grippingly fastened to the apertured surface of the base fabric.

2. The prosthesis according to claim 1, wherein the at least one base fabric has two apertured surfaces and one or more repositionable gripping fabrics are grippingly fastened to each of the two apertured surfaces.

3. The prosthesis according to claim 1, wherein the at least one base fabric is a knit.

4. The prosthesis according to claim 1, wherein the at least one barb is formed from a yarn made of a radiopaque material and constitutes the at least one radiopaque element of each repositionable gripping fabric.

5. The prosthesis according to claim 1, wherein the at least one radiopaque element includes one or more radiopaque monofilament yarns forming each gripping fabric.

6. The prosthesis according to claim 1, wherein the at least one radiopaque element is in the form of a coating made of radiopaque material deposited on at least one surface of each repositionable gripping fabric.

7. The prosthesis according to claim 1, wherein the at least one radiopaque element is in the form of a coating made of radiopaque material deposited on a surface of each of the repositionable gripping fabrics by plasma-enhanced chemical vapor deposition.

8. The prosthesis according to claim 1, wherein the plurality of repositionable gripping fabrics includes four repositionable gripping fabrics, each repositionable gripping fabric grippingly fastened to a corner of the base fabric.

9. The prosthesis according to claim 1, wherein the at least one base fabric is a three-dimensional knit.

10. A kit comprising:
at least one base fabric having at least one apertured surface which promotes penetration of cells into the base fabric and cell recolonization of the prosthesis, and,
a plurality of repositionable gripping fabrics separate from the at least one base fabric, each repositionable gripping fabric in the form of a disc having a first apertured surface, a second surface opposite the first surface, at least one radiopaque element and at least one barb projecting from the second surface of each repositionable gripping fabric, said at least one barb designed for grippingly fastening each repositionable gripping fabric to at a first specific place on the at least one apertured surface of the at least one base fabric and easily removed therefrom so as to be repositioned and refastened on a second specific place on the at least one apertured surface of the at least one base fabric, wherein each gripping fabric has an area ranging from 0.5 to 6 cm² and the first apertured surface promotes penetration of cells and preserves the cell recolonization of the prosthesis when the second surface of the gripping fabric is grippingly fastened to the apertured surface of the base fabric.

11. A prosthesis comprising:
i) at least one base fabric having at least one apertured surface which promotes penetration of cells into the base fabric and cell recolonization of the prosthesis after implantation, and
ii) a plurality of planar repositionable gripping fabrics separate from the at least one base fabric, each planar repositionable gripping fabric having a first apertured surface, a second surface opposite the first surface, at least one radiopaque element, and at least one barb projecting from the second surface of the repositionable gripping fabric and designed to grippingly fasten the second surface of the repositionable gripping fabric to a first specific place on the at least one apertured surface of the at least one base fabric and is easily removed therefrom so as to be repositioned and refastened on a second specific place on the at least one apertured surface of the at least one base fabric, wherein the first apertured surface of the gripping fabric promotes penetration of cells and preserves the cell recolonization of the prosthesis when the second surface of the gripping fabric is grippingly fastened to the apertured surface of the base fabric.

* * * * *